July 11, 1972 W. H. JESSEL, JR., ET AL Plant Pat. 3,231
CHRYSANTHEMUM PLANT
Filed Nov. 12, 1970
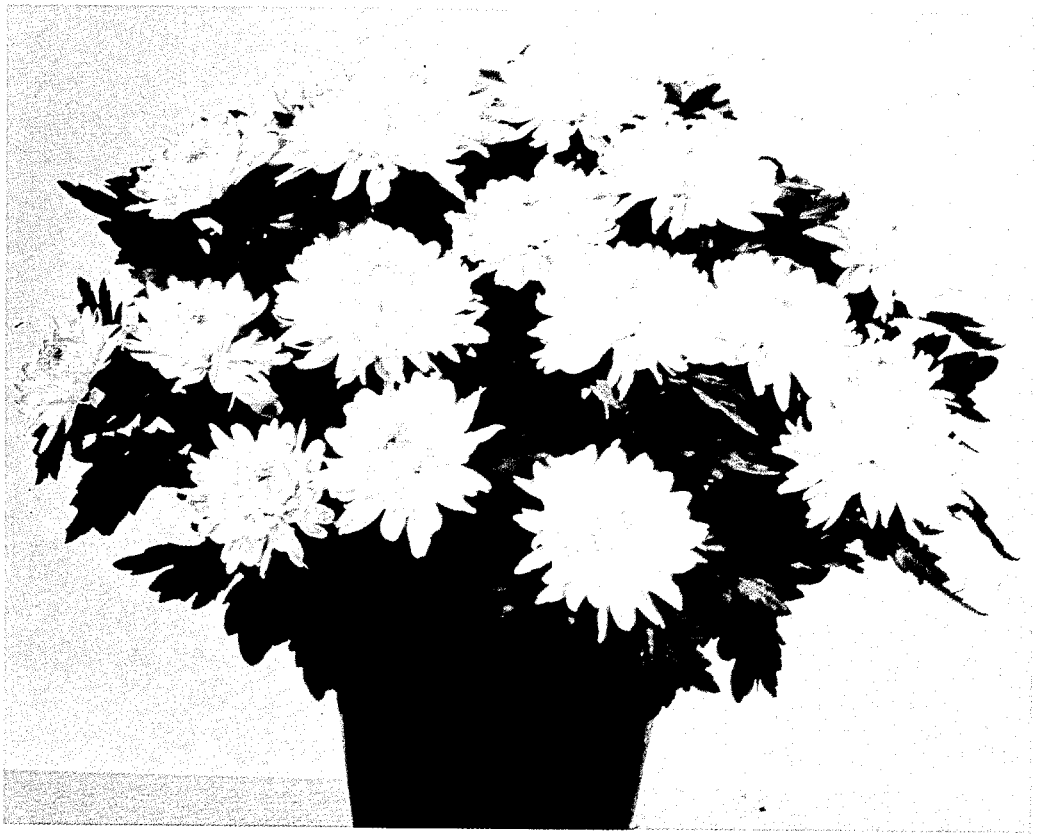
INVENTORS
WALTER H. JESSEL, Jr.
WILLIAM E. DUFFETT
BY Oberlin, Maky, Donnelly & Renner
ATTORNEYS

United States Patent Office

Plant Pat. 3,231
Patented July 11, 1972

3,231
CHRYSANTHEMUM PLANT

Walter H. Jessel, Jr., Doylestown, and William E. Duffett, Akron, Ohio, assignors to Yoder Brothers, Inc., Barberton, Ohio

Filed Nov. 12, 1970, Ser. No. 89,151
Int. Cl. A01h *5/00*
U.S. Cl. Plt.—78 1 Claim

The present invention comprises a new and distinct variety of chrysanthemum plant which is a sport of a well-known commercial and unpatented cultivar, Yellow Mandalay.

The new variety is similar in many respects to Yellow Mandalay, having the same characteristics of:

(1) Plant habit.
(2) Flower size.
(3) Period of value.

The new variety is distinguished from Yellow Mandalay by the following characteristics, when grown under identical conditions:

(1) Lighter yellow color.
(2) Does not tinge bronze during cool temperature finishes. The parent cultivar Yellow Mandalay tinges to a bronze cast at base of petal at finish temperatures in the range of 56°–58°.
(3) A three to four day faster and more uniform response during high temperature periods.
(4) Longitudinal petal roll is less during cool, low light periods.

The new variety was selected from a flowering plot of the parent variety in Barberton, Ohio, and when asexually reproduced by cuttings at Barberton, Ohio, has been found to retain its distinctive characteristics through successive propagations.

The new variety when grown in the vicinity of Barberton, Ohio, has a response period of approximately 10 weeks. The response time and blooming period may vary significantly with varying environmental conditions such as temperature, day length, and light intensity. Suggested flowering in the northern United States is March through November. In the southern United States, November through June, and in coastal California, year round.

The accompanying drawing illustrates the unique characteristics of the new variety, with the colors being as nearly true as possible with color illustrations of this type.

The following data is based on observations made of the new variety in a greenhouse in Barberton, Ohio. Color references are to the Munsell Color Book, 1963 edition, and comparisons made where relevant with the parent cultivar Yellow Mandalay.

Botanical classification: *Chrysanthemum morifolium.*

Bloom:
- *Size.*—3½" to 4".
- *Fully expanded.*—5".
- *Borne.*—Singly on disbudded branches.
- *Stems.*—Branches 10" to 16" long.
- *Form.*—Semi-incurved.
- *Permanence.*—14 to 18 days.

| | Sunny Mandalay | Yellow Mandalay |
|---|---|---|
| Color: | | |
| Center of flower | Yellow green, 8.75Y8.5/12. | Yellow green, 8.75Y8.5/12. |
| Base of petals | Yellow, 6.25Y8.5/12 | Bronze yellow, 3.75Y7/12 to yellow, 5Y8/12, depending on finishing temperatures. |
| Inside of petals | do | Bronze yellow, 3.75Y7/12 to yellow, 5Y8/12. |
| Reverse of petals | Light yellow, 7.5Y8.5/8. | Light yellow, 5Y8.5/10. |
| Tonality from a distance. | Yellow | Golden bronze to golden yellow, depending on finishing temperatures. |
| Discoloration | do | Yellow. |

Petals:
- *Texture.*—Smooth.
- *Appearance and form.*—Broadly keeled, tapering to a point.
- *Arrangement.*—Composite, whorled on a single receptacle.
- *Persistence.*—Resists shatter.
- *Fragrance.*—Typical chrysanthemum.

Reproductive organs:
- *Stamen, anthers.*—None to 30.
- *Pollen.*—None to scant.
- *Arrangement.*—Clustered in center of flower if present.
- *Styles.*—Present in both ray and disc florets.
- *Length.*—short.
- *Ovaries.*—At base of petals attached to receptacle.

Plant:
- *Form.*—Herbaceous.
- *Growth.*—Semi-upright.
- *Height,* depending on culture.—10" to 16".
- *Spread,* depending on culture.—6" to 10" as a pinched plant.

Foliage:
- *Top side.*—Dark green, 10GY2/4.
- *Size.*—5¾" long, 3¾" wide.
- *Quantity.*—Numerous.
- *Shape.*—Palmate.
- *Texture.*—Smooth.
- *Ribs and veins.*—Prominent.
- *Edge.*—Moderately indented.
- *Serration.*—Slight.
- *Underside.*—Light green, 7.5GY5/4.
- *Stipules.*—Rudimentary.

We claim:

1. A new and distinct variety of chrysanthemum characterized particularly as to uniqueness when compared with the parent cultivar Yellow Mandalay by its clear yellow color, its resistance to bronzing at low temperature finishes, its faster and more uniform response during high temperature periods, and its tendency to develop less longitudinal petal roll during low light, low temperature periods.

No references cited.

ROBERT E. BAGWILL, Primary Examiner